US009914675B2

United States Patent
Buchbinder et al.

(10) Patent No.: US 9,914,675 B2
(45) Date of Patent: *Mar. 13, 2018

(54) PROCESS FOR ALKYLATION USING IONIC LIQUID CATALYSTS

(71) Applicant: UOP LLC, Des Plaines, IL (US)

(72) Inventors: Avram M. Buchbinder, Chicago, IL (US); Douglas A. Nafis, Mount Prospect, IL (US); Alakananda Bhattacharyya, Glen Ellyn, IL (US); Susie C. Martins, Carol Stream, IL (US)

(73) Assignee: UOP LLC, Des Plaines, IL (US)

(*) Notice: Subject to any disclaimer, the term of this patent is extended or adjusted under 35 U.S.C. 154(b) by 61 days.

This patent is subject to a terminal disclaimer.

(21) Appl. No.: 14/675,203

(22) Filed: Mar. 31, 2015

(65) Prior Publication Data

US 2016/0289138 A1 Oct. 6, 2016

(51) Int. Cl.
| | |
|---|---|
| *C07C 2/60* | (2006.01) |
| *C10L 10/10* | (2006.01) |
| *C10L 1/04* | (2006.01) |
| *C10G 29/20* | (2006.01) |
| *C10L 1/06* | (2006.01) |

(52) U.S. Cl.
CPC .............. *C07C 2/60* (2013.01); *C10G 29/205* (2013.01); *C10L 1/04* (2013.01); *C10L 1/06* (2013.01); *C10L 10/10* (2013.01); *C07C 2527/125* (2013.01); *C07C 2531/02* (2013.01); *C07C 2531/22* (2013.01); *C10G 2300/305* (2013.01); *C10L 2270/00* (2013.01)

(58) Field of Classification Search
CPC . C07C 2/60; C07C 2531/02; C07C 2527/125; C07C 2531/22; C10G 29/205; C10G 2300/305; C10L 1/06; C10L 10/10; C10L 1/04; C10L 2270/00
See application file for complete search history.

(56) References Cited

U.S. PATENT DOCUMENTS

| | | | |
|---|---|---|---|
| 7,432,408 B2 | 10/2008 | Timken et al. | |
| 7,432,409 B2 | 10/2008 | Elomari et al. | |

(Continued)

FOREIGN PATENT DOCUMENTS

| | | |
|---|---|---|
| CA | 2851165 A1 | 1/2014 |

OTHER PUBLICATIONS

Tong et al. ("Surface Tension and Density of Ionic Liquid n-Butylpyridinium Heptachlorodialuminate." Journal of Chemical & Engineering Data 56.10 (2011): 3722-3724).*

(Continued)

*Primary Examiner* — Brian A McCaig
*Assistant Examiner* — Jason Y Chong (57) ABSTRACT

Alkylation processes are described. The processes utilize ionic liquid catalysts having a kinematic viscosity range of about 50 cSt to about 100 cSt at 25° C. Catalysts within this range produce alkylate having higher octane than catalysts outside this range, especially at higher process temperatures which are preferable from an operating cost standpoint. The alkylate can have one or more of a research octane number of at least about 93, a selectivity of $C_8$ of at least about 65%, and a mole ratio of trimethylpentane to dimethylhexane of greater than about 7:1.

20 Claims, 4 Drawing Sheets

(56) References Cited

U.S. PATENT DOCUMENTS

| | | | |
|---|---|---|---|
| 7,531,707 | B2 | 5/2009 | Harris et al. |
| 8,183,425 | B2 | 5/2012 | Luo et al. |
| 8,653,318 | B2 | 2/2014 | Liu et al. |
| 8,729,329 | B2 * | 5/2014 | Hommeltoft ............ C07C 2/60 585/721 |
| 8,865,960 | B2 | 10/2014 | Timken et al. |
| 2004/0133056 | A1 | 7/2004 | Liu et al. |
| 2005/0059848 | A1 | 3/2005 | Randolph et al. |
| 2007/0142676 | A1 | 6/2007 | Elomari et al. |
| 2007/0225538 | A1 | 9/2007 | Elomari |
| 2009/0166257 | A1 | 7/2009 | Luo et al. |
| 2011/0144399 | A1 | 6/2011 | Elomari et al. |
| 2012/0160740 | A1 | 6/2012 | Zhan et al. |
| 2012/0178982 | A1 | 7/2012 | Liu et al. |
| 2012/0283500 | A1 | 11/2012 | Liu et al. |
| 2013/0345484 | A1 | 12/2013 | Martins et al. |
| 2014/0113804 | A1 | 4/2014 | Martins et al. |
| 2014/0213435 | A1 | 7/2014 | Martins et al. |

OTHER PUBLICATIONS

Han et al.,"Et3NHCI-AICI3 Ionic Liquids as Catalyst for Alkylation of Toluene . . . , " China Petroleum Processing & Petrochemical Technology (2013), 15(1), 54-60.

Ochedzan-Siodlak et al., "Densities and viscosities of imidazolium and pyridinium chloroaluminate ionic liquids," Journal of Molecular Liquids (2013), v.177, 85-93.

Suxian et al.,"Research on Physical Property of the Et3NHCI/AICI3 Ionic Liquids," Guangdong Huagong Chemistry (2013), 40(13), 6-7.

Liu et al., "Reaction Performance of Isobutane Alkylation Catalyzed by a Composite Ionic Liquid at a Short Contact Time," AIChE Journal (2014), 1-10.

Wasserchild at al., "Ionic liquids in synthesis," (2008), v.1, Table 3.2-2 & Table 3.2-3.

Okoturo et al., "Temperature dependence of viscosity for room temperature ionic liquids," Journal of Electroanalytical Chemistry (2004), 568, 167-181.

International Search Report dated Aug. 18, 2016 in International Application No. PCT/US2016/024471.

* cited by examiner

PROCESS FOR ALKYLATION USING IONIC LIQUID CATALYSTS

BACKGROUND OF THE INVENTION

The alkylation of paraffins with olefins for the production of alkylate for gasolines can use a variety of catalysts. The range of suitable process conditions that result in products with high octane and desired selectivity depends on the choice of catalyst.

Ionic liquids are catalysts that can be used in a variety of catalytic reactions, including the alkylation of paraffins with olefins. Ionic liquids are primarily mixtures of salts which melt below about 100° C.

Ionic liquids comprise an organic cation and an anion where the anion is usually an inorganic anion. Ionic liquids are described in U.S. Pat. No. 4,764,440, U.S. Pat. No. 5,104,840, and U.S. Pat. No. 5,824,832 for example. The properties vary extensively for different ionic liquids depending on the cation and the anion. The use of ionic liquids depends on the properties of a given ionic liquid. In addition, the behavior of an ionic liquid may vary considerably for different temperature ranges.

Some alkylation processes utilize low temperatures, typically 10° C. or less, which generally requires chilled cooling fluid for the reactor and/or reactor feeds. This adds substantial cost in the form of additional equipment and energy usage. In some alkylation processes, isoparaffin to olefin (I/O) ratios of 20:1 or greater are used. However, high I/O ratios like these are not desirable from an operating standpoint because they increase the cost of operation, for instance, by requiring larger reactors and more energy for distillation of isoparaffin per unit of alkylate product. Some alkylation processes use ionic liquids having low viscosity (e.g., less than 25 cSt at 25° C.), such as 1-butylpyridinium heptachloroaluminate, 1-butyl-3-methylimidazolium heptachloroaluminate, and triethyl ammonium based ionic liquids. The kinematic viscosity of these ionic liquids was measured in a comparative example herein and determined to be 21.5, 15.0 and 16-19 cSt at 23-25° C. respectively. Viscosity measurements of other halometallate ionic liquids are available in literature, for instance in Okoturo, O. O; VanderNoot, T. J; *Journal of Electroanalytical Chemistry*, "Temperature dependence of viscosity for room temperature ionic liquids", 2004, vol. 568, pp. 167-181.

U.S. Pat. No. 7,432,408, U.S. Pat. No. 7,432,409, U.S. Pat. No. 7,531,707, and US 2007/0225538 broadly disclose alkylation processes using chloroaluminate ammonium, pyridinium and imidazolium ionic liquids with I/O ratios in the range of 1 to 100, catalyst volume in the reactor in the range of 2% to 70%, reaction temperatures in the range of −40° C. to 150° C., and residence times of a few seconds to a few hours. However, the Examples use low viscosity (e.g., less than 25 cSt at 25° C.) ionic liquids including 1-butylpyridinium heptachloroaluminate, and 1-butyl-3-methylimidazolium heptachloroaluminate. The viscosity of several of the ionic liquids used is unknown, including 1-butyl-4-methylpyridinium heptachloroaluminate, 1-H-pyridinium chloroaluminate, and tributyl-methyl-ammonium chloroaluminate. Based on related ionic liquids, the viscosity of 1-butyl-4-methylpyridinium heptachloroaluminate is believed to be below 40 cSt. In addition, the Examples show an I/O ratio of 4, and a temperature of 50° C. for the isopentane and ethylene alkylation. For the isopentane/propylene alkylation and isobutane/isobutene alkylation, an I/O ratio of 8, and a temperature of 10° C. were used. There are no examples for alkylation using propylene or butene at temperatures greater than 10° C., and no discussion of the problems associated with operating at those temperatures.

US 2004/0133056 describes an alkylation process utilizing alkyl-containing ammonium or pyridinium ionic liquid combined with metal compounds of Groups IB and IIB and transition metals. The broad reaction conditions include an I/O ratio of 1:1 or greater, a reaction temperature in the range of −20° C. to 100° C., and a reaction time of 2 sec to 60 min. The ionic liquids used in the Examples were low viscosity (e.g., less than 25 cSt at 25° C.) ionic liquids including triethylammonium chloroaluminates combined with copper chloride, nickel chloride, copper nitrate, and copper sulfate. Most Examples were run at low temperature (less than 10° C.: Ex. 6, 7, 11, 13, 14, 16, and 18) or high I/O ratios (30:1 or more: 10, 12, 13, 14, 16, 17, and 18). The only Examples having I/O ratios of 20:1 or less were run at low temperature (less than 10° C.: Ex. 6, 7, and 11), the reaction products had low $C_8$ content (Ex. 6-9), and/or had low TMP/DMH ratios (Ex. 6-9, 11, and 15).

US2007/0142676 describes an alkylation process for isopentane and ethylene using pyridinium-based ionic liquids. The broad conditions include a reaction temperature in the range of −20° C. to 200° C., and a reaction time of 0.1 min to 24 hr. The I/O ratio in the example was 3.2, and the ionic liquid was 1-butylpyridinium heptachloroaluminate.

US 2009/166257 describes an alkylation process utilizing chloroaluminate ammonium, pyridinium, and imidazolium ionic liquids. The broad conditions include an I/O ratio in the range of 1 to 100, a catalyst volume in the reactor of 2% to 70%, a reaction temperature in the range of −40° C. to 150° C., and a residence time of a few seconds to a few hours. The Examples showed a 1-butylpyridinium chloroaluminate ionic liquid, a catalyst volume of 10-15%, and a temperature of 0° C.

US 2012/0178982 describes the alkylation of isobutane and/or isopentane with an olefin having 2 to 8 carbons using an alkyl-containing ammonium, imidazolium, or pyridinium ionic liquid. The I/O ratio is 1:1 or greater, with high I/O ratios being preferred, e.g., at least 20:1, more preferably at least 50:1, even more preferably at least 100:1. The reaction temperature is in the range of −20° C. to 100° C. No examples are given.

US2012/0283500 describes the alkylation of isobutane and butene using alkyl-containing ammonium, imidazolium, or pyridinium ionic liquids. The examples used ionic liquids containing triethylammonium ($Et_3NH$) and 1-butyl-3-methylimidazolium cations, and anions containing chlorohexabromoaluminate or heptachloroaluminate, with some including various copper compounds. The Examples show I/O ratios of 10:1 to 40:1, and temperatures of 20° C. to 30° C. The olefin feed rate for Examples 3-8 and Comparative Examples 1-2 was calculated from the information given to be less than 0.2 g olefin/g ionic liquid/hr (1.4 mol olefin/mol ionic liquid/hr). The olefin feed rate cannot be calculated for Examples 1a-b and 2a-b because no feed rate or olefin feed rate is given for those examples. However, assuming these feed rates were the same as that in Example 4, the olefin feed rate would be less than 0.2 g olefin/g ionic liquid/hr (1.4 mol olefin/mol ionic liquid/hr). In addition, no volume fraction of ionic liquid or residence times are given.

US Application Serial Nos. 2013/0345484 and 2014/0113804 teach that certain phosphonium ionic liquids having a kinematic viscosity greater than 50 cSt at 20° C. are preferable because they result in higher octane than do lower viscosity ionic liquids, and that this advantage is larger at higher operating temperatures. However, the olefin was added with a slow flow rate (0.5 g olefin/g ionic liquid/hr or 5.2 mol olefin/mol ionic liquid/hr), leading to long residence times (e.g., about 115-120 min) Such long residence times are not desirable for commercial practice as they would require very large reactors or very small product production rates.

Therefore, an alkylation process utilizing ionic liquids that does not require operation under more extreme conditions such as refrigeration or long residence times would be desirable.

SUMMARY OF THE INVENTION

One aspect of the invention is an alkylation process. In one embodiment, the alkylation process includes passing an isoparaffin having from 4 to 10 carbon atoms to an alkylation reactor; and passing an olefin having from 3 to 10 carbon atoms to the alkylation reactor, wherein the alkylation reactor contains a haloaluminate based ionic liquid catalyst for reacting the olefin and the isoparaffin to generate an alkylate having a research octane number of at least about 93, wherein the ionic liquid catalyst has an initial kinematic viscosity in a range of about 50 cSt to about 100 cSt at a temperature of 25° C., wherein the alkylation reactor is operated at reaction conditions comprising an operating temperature greater than about 20° C., a molar ratio of isoparaffin to olefin of less than about 20:1, an overall olefin feed rate of greater than about 8 mol olefin/mol ionic liquid catalyst/hr, and a total residence time in a range of about 1 min to about 10 min.

In another embodiment, the alkylation process includes passing an isoparaffin having 4 carbon atoms to an alkylation reactor; and passing an olefin having 4 carbon atoms to the alkylation reactor, wherein the alkylation reactor contains a haloaluminate based ionic liquid catalyst for reacting the olefin and isoparaffin to generate an alkylate, wherein the ionic liquid catalyst has an initial kinematic viscosity in a range of about 50 cSt to about 100 cSt at a temperature of 25° C., wherein the alkylation reactor is operated at reaction conditions comprising an operating temperature greater than about 20° C., a molar ratio of isoparaffin to olefin of less than about 20:1, an overall olefin feed rate of greater than about 8 mol olefin/mol ionic liquid catalyst/hr, and a total residence time is in a range of about 1 min to about 10 min, wherein the reaction has a selectivity for $C_8$ of at least about 65%, and wherein the alkylate has a mole ratio of trimethylpentane to dimethylhexane of greater than about 7:1.

DETAILED DESCRIPTION OF THE INVENTION

In motor fuel alkylation processes utilizing ionic liquids as catalysts, the high viscosity of ionic liquids often results in a mass transfer limitation on the process which slows the primary reaction, leading to both decreased activity and low selectivity to the primary alkylation product. For instance, in processes using isobutane as the isoparaffin and butenes as the olefin, low $C_8$ selectivities result. On the other hand, in low viscosity ionic liquids, the isomerization of high-octane trimethylpentanes (TMP) to dimethylhexanes (DMH) is fast, leading to lower octane than with higher viscosity ionic liquids. Thus, there is an optimum catalyst viscosity for operating an ionic liquid alkylation process. Other factors such as acidity and solubility will also have an effect on activity and selectivities.

The present alkylation process operates at temperatures of about 20° C. or more and utilizes ionic liquid catalysts that have a kinematic viscosity range of about 50 cSt to about 100 cSt at 25° C., or about 50 cSt to about 95 cSt at 25° C., or about 60 cSt to about 90 cSt at 25° C. At higher operating temperatures (e.g., about 30° C. or more), the ionic liquid catalysts typically have a kinematic viscosity range of about 30 cSt to about 60 cSt at 38° C., or about 40 cSt to about 60 cSt at 38° C., or about 45 cSt to about 55 cSt at 38° C. If kinematic viscosity measurement or data is unavailable, kinematic viscosity can be approximated by dividing the dynamic viscosity of the ionic liquid in centipoise by its density in $g/cm^3$. Catalysts within this range produce alkylate having higher octane than catalysts outside this range, especially at higher process temperatures which are preferable from an operating cost standpoint.

The cation of the ionic liquid is typically a tetraalkylphosphonium cation, a 1,3-alkylimidazolium cation having long side chains (e.g., at least one of the alkyl groups contains more than about 8 carbon atoms), a pyridinium cation having at least one long alkyl side chains (e.g., a side chain with from about 5 to about 15 carbons), an ammonium cation having long side chains (e.g., longer than 4 carbon atoms), an ammonium cation having aromatic side chains, or combinations thereof.

The anionic component of the ionic liquid generally comprises a halometallate of the form $M_nX_{3n+1}$, where n is from 1 to 5; X is Cl, Br, I, or combinations thereof; and M is Al, Fe, Cu, Ni, or combinations thereof. The ionic liquid mixture can comprise a mix of the halometallates where $1 \leq n \leq 2$, and include small amount of the halometallates with n equal to 3 or greater. In some embodiments, the anionic component of the ionic liquid comprises a haloaluminate. In some embodiments, the anionic component of the ionic liquid comprises a chloroaluminate. In some embodiments the anionic component comprises a heptachloroaluminate. Here, heptachloroaluminate refers to an anion, a group of anions, or anions and aluminum chloride compounds that comprise chlorine atoms and aluminum atoms in a ratio of about 7 to about 2.

When water enters the reaction, whether brought in with a feed, or otherwise, there can be a shift, where the haloaluminate forms a hydroxide complex, or instead of $Al_nX_{3n+1}$, $Al_nA_m(OH)_x$ is formed where m+x=3n+1. However, moisture is not desirable. Ionic liquids also present some advantages over other liquid alkylation catalysts, such as being less corrosive to some materials than catalysts like HF, and being non-volatile.

Suitable ionic liquid catalysts comprise phosphonium based ionic liquids, imidazolium, pyridinium, and ammonium based ionic liquids having long side chains, imidazolium, pyridinium, or ammonium based ionic liquids having brominated anions, imidazolium, pyridinium, and ammonium based ionic liquids with halometallate anions having an anion to cation ratio greater than 1.5 and less than 2, or combinations thereof.

In some embodiments, the ionic liquid catalyst comprises tributylpentylphosphonium heptachloroaluminates, tripropylhexylphosphonium heptachloroaluminates, tributylmethylphosphonium heptachloroaluminates, benzyltrimethylammonium heptachloroaluminates, and tetrabutylphosphonium heptachloroaluminates, or combinations thereof.

The acidity needs to be controlled to provide for suitable alkylation conditions. In some embodiments, addition of a catalyst promoter, such as a Brønsted acid or a Brønsted acid precursor is employed. Suitable examples of Brønsted acid promoter are HCl or HBr although other Brønsted acids may be employed. Suitable examples of Brønsted acid precursors are haloalkanes which react in the presence of the ionic liquid to form a hydrogenhalide and an olefin. For instance, 2-chlorobutane, 2-chloro-2-methylpropane, 2-bromobutane, and 2-bromo-2-methylpropane are suitable promoters. The promoter is employed to enhance the activity of the catalyst by boosting the overall acidity of the ionic liquid-based catalyst. In some embodiments, the molar ratio of olefin to acid promoter of greater than about 15:1, or greater than about 25:1, or greater than about 30:1, or higher. The molar ratio of olefin to acid promoter is defined as the amount of olefin added to the reaction in a given period of time or present at the beginning of the period of time, divided by the amount of acid promoter fed to the reaction in the given period of time or present at the beginning of the period of time. In some embodiments, acid promoter is present in the ionic liquid itself as a result of its synthesis. This can be measured using a titration method such as titration with triethylsilane as described in Example 1 of U.S. application Ser. No. 14/270,033 "Method for quantitation of acid sites in acidic ionic liquids using silane and borane compounds."

Due to the low solubility of hydrocarbons in ionic liquids, olefins-isoparaffins alkylation, like most reactions in ionic liquids, is generally biphasic. The catalytic alkylation reaction is generally carried out in a mixed phase liquid-liquid system. The system can be a batch system, a semi-batch system, or a continuous system as is usual for aliphatic alkylation. Vigorous mixing is desirable to ensure good contact between the reactants and the catalyst.

The ionic liquid catalyst volume percent relative to the total liquid contents of the reactor is generally in the range of about 0.5% to about 45%, or less than about 40%, or less than about 35%, or less than about 30%, or less than about 25%, or less than about 20%, or less than about 15%, or less than about 10%, or less than about 5%, or less than about 4%, or less than about 3%, or less than about 2%. Volume fraction is calculated by dividing the total volume of ionic liquid in the reaction zone by the total volume of liquids, solids and supercritical fluids in the reaction zone. Volume percent is volume fraction multiplied by 100.

The isoparaffin and olefin can be introduced separately or as a mixture, in one or multiple locations. The molar ratio of isoparaffin to olefin is generally in the range of about 2:1 to about 20:1, or less than about 15:1, or less than about 13:1, or in the range of about 8:1 to about 12:1.

In a semi-batch system, the catalyst and at least a portion of the isoparaffin are introduced with no olefin present, followed by the olefin or a mixture of isoparaffin and olefin. In a semi-batch system the olefin is added gradually over a period of time. The catalyst is measured in the reactor with respect to the amount of total olefins added over the course of the reaction, with a catalyst to olefin weight ratio between 0.1:1 and 10:1, and preferably between 0.2:1 and 5:1, and more preferably between 0.4:1 and 2.5:1.

In a continuous system, the catalyst, the isoparaffin, the olefin, and optionally the catalyst promoter are each added continuously. Catalyst, optional catalyst promoter, unreacted isoparaffin, and unreacted olefin are each removed continuously from the reaction zone along with alkylate product. The catalyst, catalyst promoter, unreacted isoparaffin, and/or unreacted olefin may be recycled. The olefin may be added to one or more locations in the reaction zone. It is preferable to add the olefin to multiple locations in the reaction zone. Adding olefin in multiple locations, or spreading the olefin addition over a longer period of time results in the isoparaffin to olefin ratio measured in a specific location at a specific point in time to be higher. The isoparaffin to olefin ratio is defined as the cumulative amount of isoparaffin divided by the cumulative amount of olefin added across the entire reaction zone.

The overall olefin feed rate is typically at least about 8 mol olefin/mol ionic liquid/hr, or at least about 12 mol olefin/mol ionic liquid/hr, or at least about 16 mol olefin/mol ionic liquid/hr, or at least about 20 mol olefin/mol ionic liquid/hr, or at least about 25 mol olefin/mol ionic liquid/hr, or at least about 30 mol olefin/mol ionic liquid/hr, or at least about 35 mol olefin/mol ionic liquid/hr, or at least about 40 mol olefin/mol ionic liquid/hr, or at least about 45 mol olefin/mol ionic liquid/hr, or at least about 50 mol olefin/mol ionic liquid/hr, or at least about 55 mol olefin/mol ionic liquid/hr, or at least about 60 mol olefin/mol ionic liquid/hr, or at least about 75 mol olefin/mol ionic liquid/hr, or at least about 100 mol olefin/mol ionic liquid/hr, or at least about 125 mol olefin/mol ionic liquid/hr, or at least about 150 mol olefin/mol ionic liquid/hr, or at least about 175 mol olefin/mol ionic liquid/hr, or at least about 200 mol olefin/mol ionic liquid/hr, or at least about 225 mol olefin/mol ionic liquid/hr, or at least about 250 mol olefin/mol ionic liquid/hr. In a batch or semibatch process, the moles of ionic liquid is measured as the total amount of ionic liquid in the reactor. In a semibatch process, the moles of olefin per hour is measured as the total molar flow rate of olefin added to the reactor per hour. In a batch process, the moles of olefin per hour is measured as the total moles of olefin added to the reactor divided by the total reaction time. In a continuous process, the olefin feed rate is measured as the total molar flow rate of olefin divided by the total molar flow rate of ionic liquid divided by the overall liquid residence time.

In some embodiments, olefin may be added to several locations in the reaction zone. The overall olefin feed rate is defined as the sum of all olefin flows added to the reaction zone.

Advantageously, the process does not require cooling below environmental temperatures or conditions. The process is operated at temperatures greater than about 20° C. The reaction temperature is generally in the range about 20° C. to about 100° C., or about 20° C. to about 70° C. In some embodiments, the operating temperature is in the range of about 20° C. to about 30° C. In other embodiments, the operating temperature is greater than about 30° C., or in the range about 30° C. to about 100° C., or about 30° C. to about 70° C. As the temperature of the operation increases, it is preferred that the kinematic viscosity of the ionic liquid does not drop too sharply. It is desirable that the ionic liquid has a kinematic viscosity of about 30 to about 60 cSt at 38° C., or about 40 to about 60 cSt at 38° C. The alkylation reaction is exothermic. In some embodiments, the heat of reaction is removed by heat exchange with a cooling fluid. Operation of the reaction at temperatures greater than 30° C. may be desired in order to reduce the cost of chilling the cooling fluid.

The pressure can be in the range from atmospheric pressure to 8000 kPa, preferably sufficient to keep the reactants in the liquid phase. For example, when isobutane is used, the pressure is desirably at least about 340 kPa (g) (35 psig) at 20° C. in order to maintain the isobutane in the liquid phase.

The total residence time of reactants in the vessel is generally in the range of about 1 min to about 10 min, or about 2 min to about 8 minutes.

The heat generated by the reaction can be eliminated using any of the methods known to those of skill in the art.

At the reactor outlet, the hydrocarbon phase is separated from the ionic liquid phase by gravity settling based on density differences, or by other separation techniques known to those skilled in the art. Then the hydrocarbons are separated by distillation, and the starting isoparaffin which has not been converted is recycled to the reactor. The catalyst is typically recycled to the reactor as well.

Typical alkylation conditions may include a catalyst volume in the reactor of from about 1 vol % to about 50 vol %, a temperature of from about 20° C. to about 70° C., a pressure of from about 340 kPa(g) to about 5000 kPa(g), an isobutane to olefin molar ratio of from about 2 to about 20, and a total residence time of about 1 min to about 10 min.

In some embodiments, the research octane number of the alkylate is at least about 93, or at least about 94, or at least about 95.

The conversion of the olefin is typically at least about 96%, or at least about 97%, or at least about 98%, or at least about 99%. The percent olefin conversion is defined as (the amount of olefin added to the reactor minus the amount of olefin remaining after the reaction (or at the reactor outlet)) divided by the total amount of olefin added to the reactor times 100. In a continuous process, olefin conversion is defined as (the amount of olefin added to the reactor minus the total flow of olefin out of the reactor) divided by the total flow of olefin into the reactor.

The alkylation process is intended to include the upgrading of lower value hydrocarbons to higher value hydrocarbon products. The preferred alkylation reaction is to react isoparaffins having from 4 to 10 carbon atoms, typically 4 to 5 carbon atoms, more typically 4 carbon atoms, with olefins having from 3 to 10 carbon atoms, typically from 3 to 5 carbon atoms, more typically 4 carbon atoms. The feed streams of isoparaffins and olefins are generally mixtures containing more than one carbon number. For example, an isobutane stream may also contain other paraffins and isoparaffins such as propane, normal butane, isopentane, etc., typically in amounts of less than about 20%. Thus, a stream containing isoparaffins or olefins having 4 carbon atoms will typically contain about 80% or more of isoparaffins or olefins having 4 carbon atoms, and about 20% or less of isoparaffins or olefins having 5 or more carbons or 3 or less carbons.

In some embodiments, the process can be used to upgrade low value $C_4$ hydrocarbons to higher value alkylates. To that extent, one specific embodiment is the alkylation of isobutane with butenes to generate $C_8$ compounds. Preferred products include isomers of trimethylpentane (TMP), namely 2,2,3-trimethylpentane, 2,2,4-trimethylpentane, 2,3,3-trimethylpentane, and 2,3,4-trimethylpentane. Other $C_8$ isomers are also produced. One set of competing isomers are dimethylhexanes (DMH), namely 2,2-dimethylhexane, 2,3-dimethylhexane, 2,4-dimethylhexane, 2,5-dimethylhexane, 3,3-dimethylhexane, and 3,4-dimethylhexane. The quality of the product stream can be measured in the ratio of total TMP to total DMH, with a higher ratio desired, e.g. of greater than about 7:1, or greater than about 10:1, or greater than about 12:1, or greater than about 14:1.

In some embodiments, the alkylation process for butanes and butenes is operated at a temperature greater than about 20° C. In some embodiments, the reaction can have a selectivity for $C_8$ of at least about 65% or more. Selectivity for $C_8$ is defined here as the total weight of products containing exactly eight carbon atoms divided by the total weight of products containing five or more carbon atoms. In some embodiments, the alkylate can have a mole ratio of trimethylpentane to dimethylhexane of greater than about 7:1, or greater than about 10:1, or greater than about 12:1 or greater than about 14:1.

In some embodiments, the alkylation process for butanes and butenes is operated at a temperature a range of about 20° C. to about 30° C. In some embodiments, the reaction can have a selectivity for $C_8$ of at least about 67%. In some embodiments, the alkylate can have a mole ratio of trimethylpentane to dimethylhexane of greater than about 12:1. In some embodiments, the alkylate can have a research octane number of at least about 95.

In some embodiments, the alkylation process for butanes and butenes is operated at a temperature greater than about 30° C. In some embodiments, the reaction has a selectivity for $C_8$ of at least about 65%. In some embodiments, the alkylate has a mole ratio of trimethylpentane to dimethylhexane of greater than about 7:1.

EXAMPLES

Comparative Example 1

Viscosity of Ionic Liquids

Figure 1:
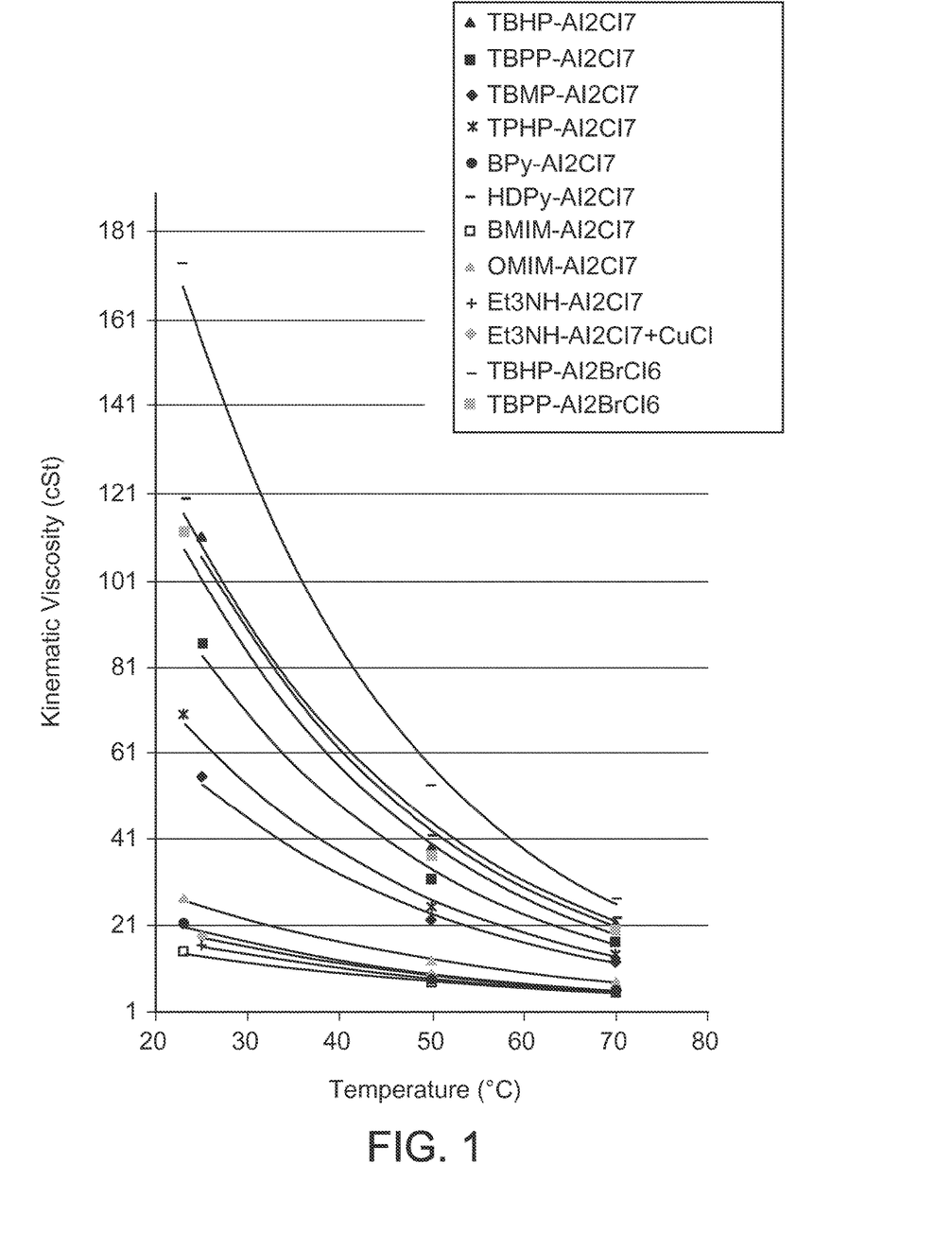
FIG. 1 is a graph showing the kinematic viscosity of various ionic liquids at different temperatures.

Phosphonium based ionic liquids were prepared by methods analogous to those described in Example 1 of US Publication No. 2013/0345484. Other ionic liquids were prepared similarly from appropriate precursors. Tributylhexylphosphonium heptachloroaluminate (TBHP-$Al_2Cl_7$) was prepared from tributylhexylphosphonium chloride with addition of two molar equivalents of $AlCl_3$; 1-butylpyridinium heptachloroaluminate (BPy-$Al_2Cl_7$) was prepared from 1-butylpyridinium chloride with addition of two molar equivalents of $AlCl_3$; 1-hexadecylpyridinium heptachloroaluminate (HDPy-$Al_2Cl_7$) was prepared from 1-hexadecylpyridinium chloride with addition of two molar equivalents of $AlCl_3$; 1-butyl-3-methylimidazolium heptachloroaluminate (BMIM-$Al_2Cl_7$) was prepared from 1-butyl-3-methylimidazolium chloride with addition of two molar equivalents of $AlCl_3$; tributylpentylphosphonium bromohexachloroaluminate (TBPP-$Al_2BrCl_6$) was prepared from tributylpentylphosphonium bromide with addition of two molar equivalents of $AlCl_3$, and tributylpentylphosphonium bromohexachloroaluminate (TBPP-$Al_2BrCl_6$) was prepared from tributylpentylphosphonium bromide with addition of two molar equivalents of $AlCl_3$. Aluminum chloride addition was initiated at a temperature between room temperature and 70° C. in order to liquefy the chloride or bromide reactant. When synthesis was conducted on larger scale, it was done in a reactor with a cooling jacket, and the temperature of the exothermic reaction was maintained below 120° C. The kinematic viscosity of each ionic liquid was measured at three temperatures. The Results are shown below in Table 1 and in FIG. 1 for a representative sample of each of the ionic liquids. An exponential curve was fit to each set of viscosity measurements and used to determine approximate viscosity at temperatures that were not measured directly.

Example 1

Viscosity of Ionic Liquids

Phosphonium based ionic liquids were prepared by methods analogous to those described in Example 1 of US Publication No. 2013/0345484. Tributylpentylphosphonium heptachloroaluminate (TBPP-$Al_2Cl_7$) was prepared from tributylpentylphosphonium chloride with addition of two molar equivalents of $AlCl_3$; tributylmethylphosphonium heptachloroaluminate (TBMP-$Al_2Cl_7$) was prepared from tributylmethylphosphonium chloride with addition of two molar equivalents of $AlCl_3$; and tripropylhexylphosphonium heptachloroaluminate (TPHP-$Al_2Cl_7$) was prepared from tripropylhexylphosphonium chloride with addition of two molar equivalents of $AlCl_3$. Aluminum chloride addition was initiated at a temperature between room temperature and 70° C. in order to liquefy the chloride or bromide reactant. When synthesis was conducted on larger scale, it was done in a reactor with a cooling jacket and temperature of the exothermic reaction was maintained below 120° C. The kinematic viscosity of each ionic liquid was measured at three temperatures. The Results are shown below in Table 1 and in FIG. 1 for a representative sample of each of the ionic liquids. An exponential curve was fit to each set of viscosity measurements and used to determine approximate viscosity at temperatures that were not measured directly. We did not measure the viscosity of benzyltrimethylammonium heptachloroaluminate and tetrabutylphosphonium heptachloroaluminate, but the dynamic viscosities of these ionic liquids are reported in Okoturo, O. O; VanderNoot, T. J; *Journal of Electroanalytical Chemistry*, "Temperature dependence of viscosity for room temperature ionic liquids," 2004, vol. 568, pp. 167-181. Their measurements are 64 centipoise and 90 centipoise respectively.

TABLE 1

Kinematic viscosity of several ionic liquids at various temperatures

| Ionic liquid | Temperature (° C.) | Viscosity (cSt) |
|---|---|---|
| TBHP-$Al_2BrCl_6$ | 23 | 173.7 |
| | 50 | 53.5 |
| | 70 | 27.2 |
| TBPP-$Al_2Cl_7$ | 25 | 86.2 |
| | 50 | 31.86 |
| | 70 | 17.40 |
| TBPP-$Al_2BrCl_6$ | 23 | 112.1 |
| | 50 | 37.07 |
| | 70 | 19.98 |
| TPHP-$Al_2Cl_7$ | 23 | 69.79 |
| | 50 | 25.3 |
| | 70 | 14.30 |
| BMIM-$Al_2Cl_7$ | 23 | 14.95 |
| | 50 | 7.79 |
| | 70 | 5.6 |
| BPy-$Al_2Cl_7$ | 23 | 21.54 |
| | 50 | 8.79 |
| | 70 | 6.0 |
| OMIM-$Al_2Cl_7$ | 23 | 27.28 |
| | 50 | 12.83 |
| | 70 | 8.00 |
| HDPy-$Al_2Cl_7$ | 23 | 119.8 |
| | 50 | 41.83 |
| | 70 | 22.95 |
| TBHP-$Al_2Cl_7$ | 25 | 111.1 |
| | 50 | 39.14 |
| | 70 | 22.02 |
| TBMP-$Al_2Cl_7$ | 25 | 55.41 |
| | 50 | 22.34 |
| | 70 | 12.74 |

TABLE 1-continued

Kinematic viscosity of several ionic liquids at various temperatures

| Ionic liquid | Temperature (° C.) | Viscosity (cSt) |
|---|---|---|
| $Et_3NH$—$Al_2Cl_7$ | 25 | 16.36 |
| | 50 | 8.32 |
| | 70 | 5.56 |
| $Et_3NH$—$Al_2Cl_7$ + 0.19 mol CuCl | 25 | 18.43 |
| | 50 | 9.279 |
| | 70 | 6.092 |

Example 2

Acidity Measurements

The density of Brønsted acid sites in fresh ionic liquid batches was determined by titration with triethylsilane according to the methods in described in U.S. application Ser. No. 14/270,033 "Method for quantitation of acid sites in acidic ionic liquids using silane and borane compounds." The results for each ionic liquid batch used in example two are shown in Table 2, along with the total amount of acid sites per mole of ionic liquid. The total number of acid sites per mole of ionic liquid is calculated by summing the number of moles of triethylsilane converted per gram of ionic liquid titrated in the acidity measurement, and the amount of moles of 2-chlorobutane added in the experiment.

Example 3

Alkylation Testing

Figure 2:
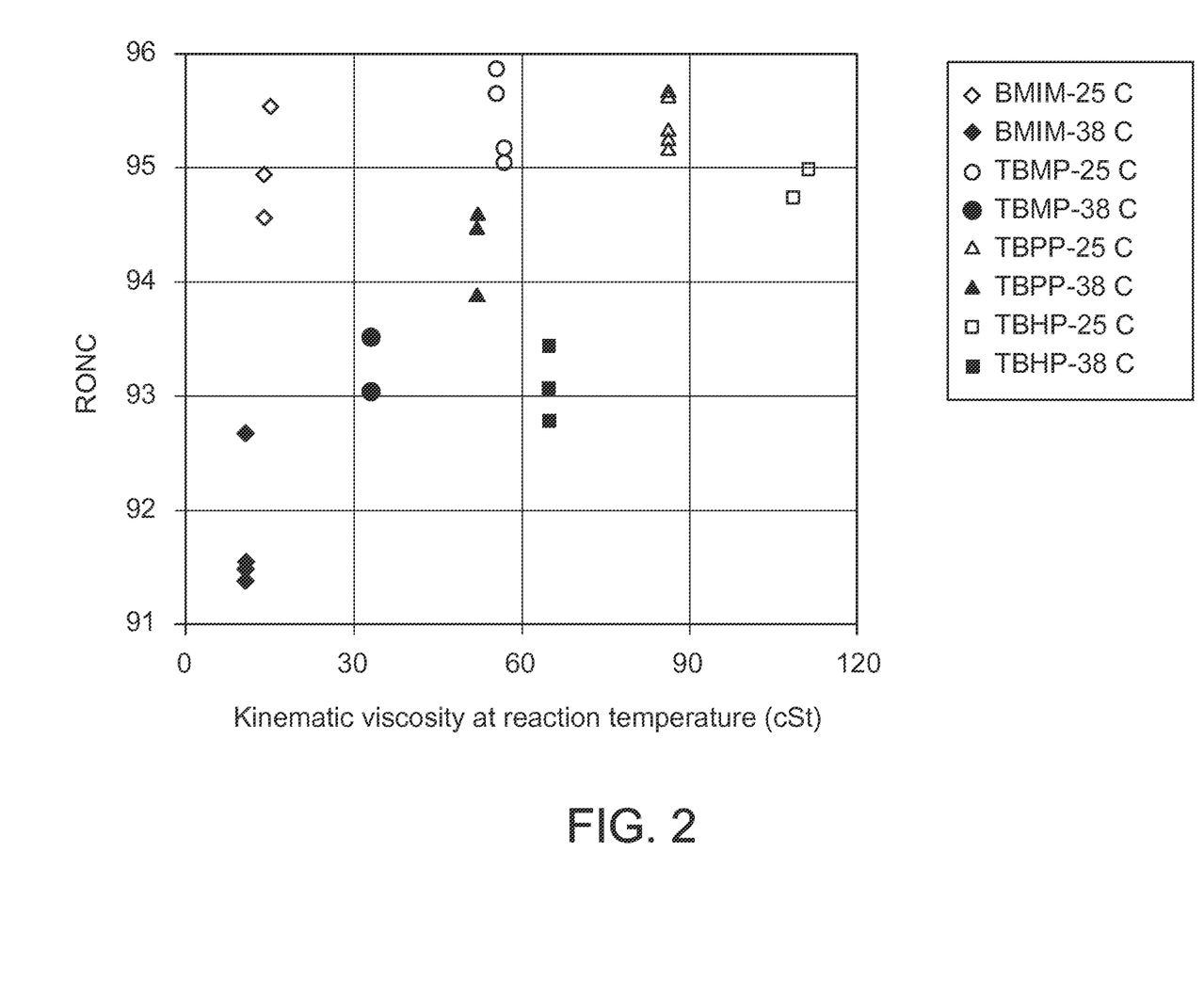
FIG. 2 is a graph showing the research octane number as a function of the kinematic viscosity for various ionic liquids at different temperatures.
Figure 3:
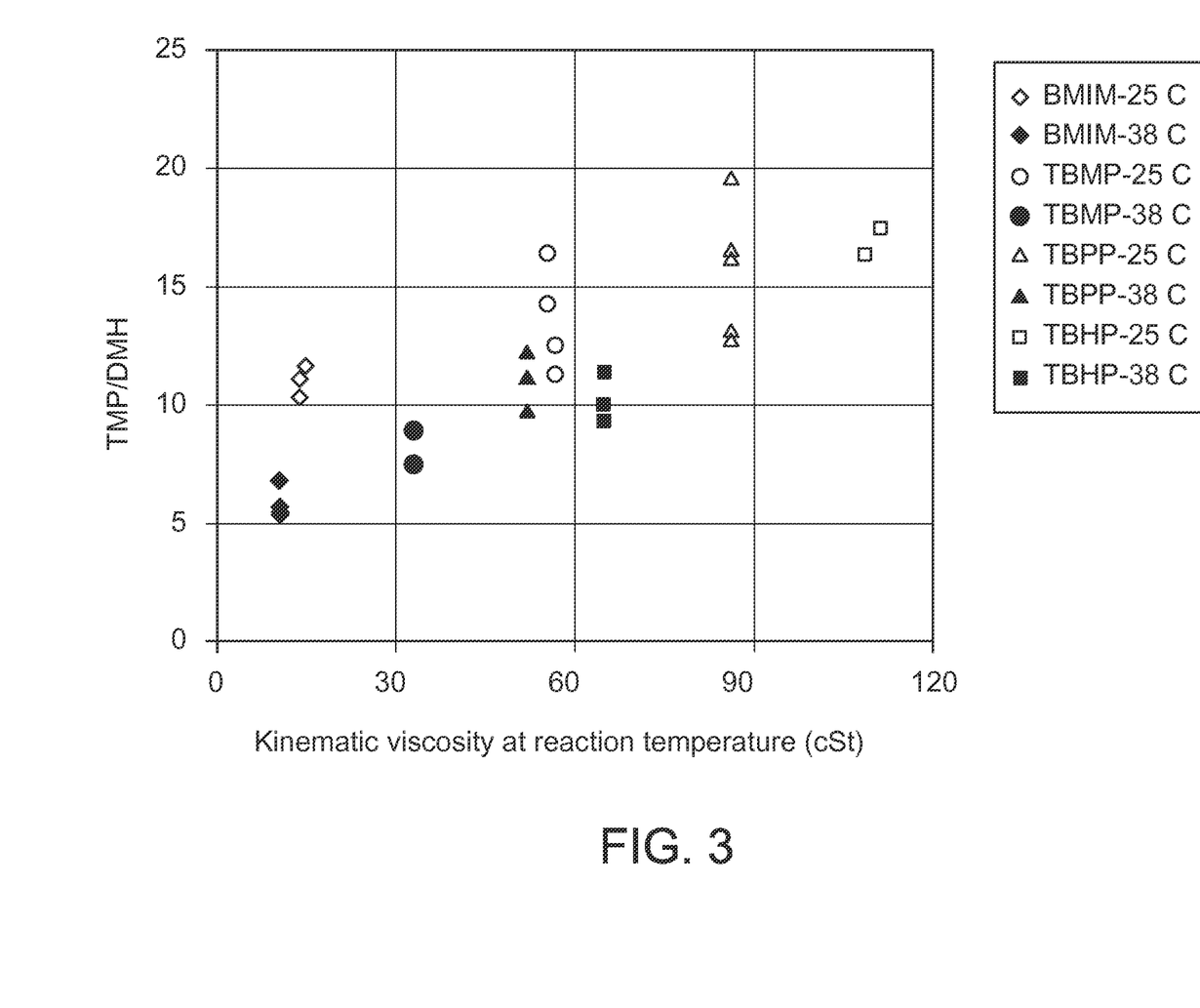
FIG. 3 is a graph showing the ratio of trimethylpentane to dimethylhexane as a function of the kinematic viscosity for various ionic liquids at different temperatures.
Figure 4:
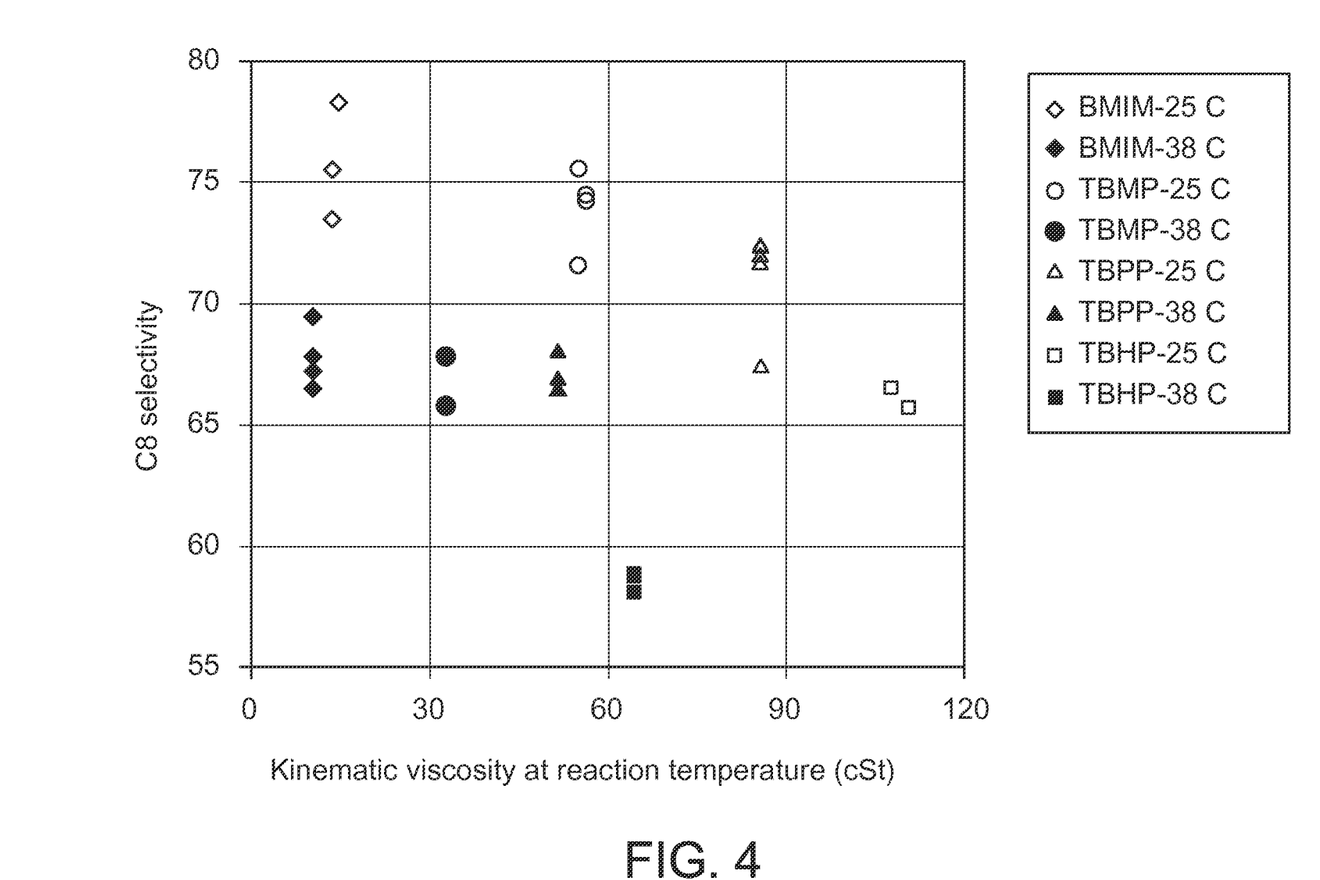
FIG. 4 is a graph showing $C_8$ selectivity as a function of the kinematic viscosity for various ionic liquids at different temperatures.

Four types of ionic liquids, TBHP-$Al_2Cl_7$, TBPP-$Al_2Cl_7$, TBMP-$Al_2Cl_7$, and BMIM-$Al_2Cl_7$ were tested as catalysts for isobutane alkylation with 2-butenes. Here, TBHP-$Al_2Cl_7$, and BMIM-$Al_2Cl_7$ serve as comparative examples. The conditions of each run are found in Table 2. About 8 g of ionic liquid was loaded in a 300 cc autoclave with an amount of 2-chlorobutane (used as a catalyst promoter). The autoclave was fitted with a Cowles-type impeller. 80 g of isobutane was charged and the reactor was pressurized to about 3.4 MPa(g) (500 psig) with nitrogen. After pressurizing the reactor, the mixture was stirred at 1700-1900 rpm for 20 minutes to ensure breakdown of 2-chlorobutane. The reactor was heated to the desired temperature, mixing at 1700 to 1900 RPM was resumed, and the reaction was initiated by the addition of approximately 8 g of 2-butenes (mixed cis- and trans-isomers), over the course of 2.5 minutes. The 2-butenes blend also contained about 8 wt % n-pentane that was used as a tracer to verify the amount of butenes added. Mixing was stopped, and the mixture was allowed to settle. The hydrocarbon was analyzed by gas chromatography (GC). The experiments were repeated several times, and in some cases with different batches of the same ionic liquid. For each batch and temperature, the amount of 2-chlorobutane was adjusted in repeat experiments until the optimal $C_8$ selectivity and octane was obtained. Table 2 also shows results for these experiments. The alkylate research octane number, TMP/DMH ratio and $C_8$ selectivity for these examples are also shown in FIGS. 2-4 respectively. The calculation for selectivity for $C_5$, $C_6$, $C_7$, and $C_{9+}$ is similar to the calculation for $C_8$ selectivity.

Comparative Example 2

Two ionic liquids, TBPP-$Al_2Cl_7$ and Et3NH-$Al_2Cl_7$+0.19 mol CuCl were tested at the same conditions as example 3, but with a high I/O ratio of about 20:1. This was done by decreasing the olefin flow rate such that addition of olefin over the course of 2.5 minutes resulted in addition of only 3.9 g of isobutane and the higher cumulative I/O ratio. Conditions and results for these examples are shown in Table 3.

Example 4

TBPP-$Al_2Cl_7$ catalyst was tested for isobutane alkylation with 2-butenes but with longer residence time and less ionic liquid than the tests in example 2. 6 g of ionic liquid was loaded in a 300 cc autoclave with 0.62 g of 2-chlorobutane. The autoclave was fitted with a Cowles-type impeller. 80 g of isobutane was charged, and the reactor was pressurized to about 3.4 MPa(g) (500 psig) with nitrogen. After pressurizing the reactor the mixture was stirred at 1700-1900 rpm for 20 minutes to ensure breakdown of 2-chlorobutane. With continued mixing, the reaction was initiated at 25° C. by the addition of 7.25 g of 2-butenes (mixed cis- and trans-isomers) over the course of 8 minutes. The 2-butenes blend also contained about 8 wt % n-pentane that was used as a tracer to verify the amount of butenes added. Mixing was stopped, and the mixture was allowed to settle. The hydrocarbon was analyzed by GC. Analysis of the product showed 99.5% conversion of butenes, 96.46 calculated research octane, TMP/DMH of 16.9, $C_5$ selectivity of 4.7%, $C_6$ selectivity of 4.8%, $C_7$ selectivity of 4.0%, $C_8$ selectivity of 78.2%, and $C_{9+}$ selectivity of 8.25%.

TABLE 2

Conditions and results for isobutane alkylation with 2-butenes

| | Example | | | | | | | | |
|---|---|---|---|---|---|---|---|---|---|
| | 3a | 3b | 3c | 3d | 3e | 3f | 3g | 3h | 3i |
| Ionic Liquid cation (All $Al_2Cl_7$ anion) | BMIM | BMIM | BMIM | TBHP | TBHP | TBMP | TBMP | TBMP | TBMP |
| IL Viscosity cSt* | 15.00 | 13.98 | 13.98 | 111.10 | 108.40 | 56.80 | 56.80 | 55.41 | 55.41 |
| IL loading, grams | 8 | 8 | 8 | 8 | 8 | 8 | 8 | 8 | 8 |
| grams 2-Chlorobutane | 0.23 | 0.503 | 0.401 | 0.242 | 0.66 | 0.375 | 0.375 | 0.421 | 0.421 |
| g of $C_4=$ | 7.14 | 7.82 | 8.04 | 6.85 | 7.65 | 7.87 | 7.15 | 6.65 | 7.82 |
| Olefin feed rate (mol $C_4=$/mol IL/hr) | 169 | 186 | 190 | 216 | 241 | 219 | 199 | 185 | 217 |
| Isoparaffin/olefin | 10.8 | 9.88 | 9.6 | 11.3 | 10.1 | 9.9 | 10.9 | 12.19 | 9.8894 |
| Titration mol TESi/g IL** | 9.27E−5 | 3.87E−5 | 3.87E−5 | 8.19E−5 | 9.68E−6 | 1.67E−5 | 1.67E−5 | 1.15E−4 | 1.67E−5 |
| Total acid mol/mol IL | 0.180 | 0.320 | 0.256 | 0.241 | 0.531 | 0.272 | 0.272 | 0.356 | 0.304 |
| Reaction time (min) | 2.5 | 2.5 | 2.5 | 2.5 | 2.5 | 2.5 | 2.5 | 2.50 | 2.5 |
| Temp, ° C. | 25 | 25 | 25 | 25 | 25 | 25 | 25 | 25 | 25 |
| Impeller diameter (inches) | 1.25 | 1.5 | 1.5 | 1.5 | 1.5 | 1.5 | 1.25 | 1.5 | 1.5 |
| Butenes Conversion (%) | 100.0 | 99.9 | 99.9 | 99.9 | 100.0 | 99.6 | 99.9 | 99.9 | 99.9 |
| Research octane (calculated) | 95.5 | 94.6 | 94.9 | 95.0 | 94.7 | 95.0 | 95.2 | 95.9 | 95.6 |
| TMP/DMH ratio | 11.6 | 10.3 | 11.1 | 17.5 | 16.4 | 11.3 | 12.5 | 14.3 | 16.4 |
| wt % $C_5$ Selectivity*** | 6.0 | 7.7 | 6.8 | 6.0 | 6.1 | 7.5 | 7.0 | 5.8 | 6.1 |
| wt % $C_6$ Selectivity*** | 4.5 | 5.3 | 5.1 | 7.1 | 7.1 | 4.5 | 4.8 | 5.1 | 6.2 |
| wt % $C_7$ Selectivity*** | 4.1 | 4.5 | 3.9 | 5.6 | 5.4 | 4.5 | 4.4 | 4.8 | 4.8 |
| Wt % $C_8$ Selectivity*** | 78.3 | 73.5 | 75.5 | 65.8 | 66.6 | 74.3 | 74.5 | 75.6 | 71.6 |
| wt % $C_9+$ Selectivity*** | 7.1 | 9.0 | 8.7 | 15.5 | 14.8 | 9.2 | 9.3 | 8.6 | 11.3 |

| | Example | | | | | | | | |
|---|---|---|---|---|---|---|---|---|---|
| | 3j | 3k | 3l | 3m | 3n | 3o | 3p | 3q | 3r |
| Ionic Liquid cation (All $Al_2Cl_7$ anion) | TBPP | TBPP | TBPP | TBPP | TBPP | BMIm | BMIM | BMIM | BMIM |
| IL Viscosity cSt* | 86.20 | 86.20 | 86.79 | 83.81 | 83.81 | 10.62 | 10.62 | 10.62 | 10.62 |
| IL loading, grams | 8 | 8 | 8 | 8 | 8 | 8 | 8 | 8 | 8 |
| grams 2-Chlorobutane | 0.329 | 0.455 | 0.499 | 0.503 | 0.422 | 0.5 | 0.5 | 0.499 | 0.401 |
| g of $C_4=$ | 6.99 | 7.50 | 6.82 | 8.17 | 7.95 | 7.67 | 7.27 | 7.92 | 8.08 |
| Olefin feed rate (mol $C_4=$/mol IL/hr) | 215 | 231 | 210 | 252 | 245 | 181 | 172 | 188 | 192 |
| Isoparaffin/olefin | 11 | 10.30 | 11.61 | 9.45 | 9.71 | 9.9 | 10.62 | 9.8 | 9.7 |
| Titration mol TESi/g IL** | 3.5E−6 | 3.5E−6 | 3.26E−5 | 1.74E−5 | 1.74E−5 | 3.87E−5 | 3.87E−5 | 3.87E−5 | 3.87E−5 |
| Total acid mol/mol IL | 0.258 | 0.357 | 0.407 | 0.402 | 0.339 | 0.316 | 0.316 | 0.316 | 0.258 |
| Reaction time (min) | 2.5 | 2.50 | 2.5 | 2.5 | 2.5 | 2.5 | 2.5 | 2.5 | 2.5 |
| Temp, ° C. | 25 | 25 | 25 | 25 | 25 | 38 | 38 | 38 | 38 |
| Impeller diameter (inches) | 1.5 | 1.5 | 1.5 | 1.5 | 1.5 | 1.5 | 1.5 | 1.5 | 1.5 |
| Butenes Conversion (%) | 100.0 | 99.9 | 99.9 | 99.9 | 99.9 | 100.0 | 97.2 | 99.9 | 100.0 |
| Research octane (calculated) | 95.6 | 95.3 | 95.2 | 95.7 | 95.1 | 91.5 | 91.4 | 91.5 | 92.7 |
| TMP/DMH ratio | 16.4 | 19.4 | 13.0 | 16.0 | 12.6 | 5.6 | 5.5 | 5.7 | 6.8 |
| wt % $C_5$ Selectivity*** | 5.8 | 5.9 | 6.8 | 6.2 | 6.8 | 11.0 | 11.3 | 11.2 | 9.4 |
| wt % $C_6$ Selectivity*** | 5.5 | 6.6 | 5.9 | 6.2 | 5.8 | 6.2 | 6.1 | 6.4 | 5.8 |
| wt % $C_7$ Selectivity*** | 4.7 | 5.3 | 5.1 | 5.1 | 5.1 | 5.7 | 5.8 | 5.6 | 5.7 |
| Wt % $C_8$ Selectivity*** | 72.4 | 67.4 | 72.0 | 71.8 | 72.3 | 67.3 | 67.9 | 66.5 | 69.5 |

TABLE 2-continued

Conditions and results for isobutane alkylation with 2-butenes

| wt % $C_9$+ Selectivity*** | 11.6 | 14.8 | 10.2 | 10.8 | 10.1 | 9.8 | 8.9 | 10.3 | 9.6 |
|---|---|---|---|---|---|---|---|---|---|

| | Example | | | | | | | |
|---|---|---|---|---|---|---|---|---|
| | 3s | 3t | 3u | 3v | 3w | 3x | 3y | 3z |
| Ionic Liquid cation (All $Al_2Cl_7$ anion) | TBHP | TBHP | TBHP | TBMP | TBMP | TBPP | TBPP | TBPP |
| IL Viscosity cSt* | 64.83 | 64.83 | 64.83 | 33.0 | 33.0 | 52.0 | 52.0 | 48.39 |
| IL loading, grams | 8 | 8 | 8 | 8 | 8 | 8 | 8 | 8 |
| grams 2-Chlorobutane | 0.66 | 0.67 | 0.805 | 0.382 | 0.42 | 0.329 | 0.329 | 0.331 |
| g of $C_4$= | 7.80 | 7.56 | 7.34 | 5.26 | 7.68 | 6.83 | 7.24 | 8.06 |
| Olefin feed rate (mol $C_4$=/mol IL/hr) | 246 | 238 | 231 | 146 | 214 | 210 | 223 | 248 |
| Isoparaffin/olefin | 9.9 | 10.22 | 10.5 | 12.5 | 10.06 | 11.4 | 10.9 | 9.58 |
| Titration mol TESi/g IL** | 9.68E−6 | 9.68E−6 | 9.68E6 | 1.67E−5 | 1.15E−4 | 4E−06 | 3.5E−6 | 1.74E−5 |
| Total acid mol/mol IL | 0.531 | 0.539 | 0.646 | 0.277 | 0.355 | 0.258 | 0.258 | 0.268 |
| Reaction time (min) | 2.5 | 2.5 | 2.5 | 2.5 | 2.50 | 2.5 | 2.5 | 2.5 |
| Temp, ° C. | 38 | 38 | 38 | 38 | 38 | 38 | 38 | 38 |
| Impeller diameter (inches) | 1.5 | 1.5 | 1.5 | 1.5 | 1.5 | 1.5 | 1.5 | 1.5 |
| Butenes Conversion (%) | 99.9 | 100.0 | 100.0 | 99.9 | 99.9 | 99.5 | 99.9 | 100.0 |
| Research octane (calculated) | 92.8 | 93.4 | 93.1 | 93.0 | 93.5 | 94.6 | 94.5 | 93.9 |
| TMP/DMH ratio | 9.3 | 11.4 | 10.1 | 7.5 | 9.0 | 12.2 | 11.1 | 9.7 |
| wt % $C_5$ Selectivity*** | 9.8 | 8.9 | 9.5 | 10.8 | 8.7 | 7.6 | 8.2 | 8.5 |
| wt % $C_6$ Selectivity*** | 8.0 | 8.0 | 8.3 | 5.4 | 6.5 | 6.4 | 6.4 | 6.4 |
| wt % $C_7$ Selectivity*** | 7.2 | 7.1 | 7.2 | 6.4 | 7.1 | 6.3 | 6.3 | 6.3 |
| Wt % $C_8$ Selectivity*** | 58.2 | 59.0 | 58.9 | 67.9 | 65.9 | 66.4 | 68.0 | 66.9 |
| wt % $C_9$+ Selectivity*** | 16.8 | 17.0 | 16.2 | 9.5 | 11.9 | 13.2 | 11.1 | 11.9 |

*kinematic viscosity of IL at reaction temperature as determined by example 1 or comparative example 1
**measure of Brønsted acid sites in fresh IL before 2-chlorobutane addition
***selectivities as wt % of $C_{5+}$ products

TABLE 3

| Example | Comp 2a | Comp 2b |
|---|---|---|
| Ionic Liquid | TBPP-$Al_2Cl_7$ | $Et_3NH$—$Al_2Cl_7$ + 0.19 mol CuCl |
| IL Viscosity cSt* | 48.39 | 12.95 |
| IL loading, grams | 8 | 8 |
| grams 2-Chlorobutane | 0.304 | 0.334 |
| g of $C_4$= | 3.88 | 3.93 |
| Isoparaffin/olefin | 19.9 | 19.6 |
| Reaction time (min) | 2.5 | 2.5 |
| Temp, ° C. | 38 | 38 |
| Impeller diameter (inches) | 1.5 | 1.5 |
| Butenes Conversion (%) | 100.0 | 100.0 |
| Research octane (calculated) | 91.8 | 89.6 |
| TMP/DMH ratio | 5.04 | 3.89 |
| wt % $C_5$ Selectivity*** | 8.70 | 12.29 |
| wt % $C_6$ Selectivity*** | 4.88 | 5.85 |
| wt % $C_7$ Selectivity*** | 4.99 | 5.30 |
| Wt % $C_8$ Selectivity*** | 75.01 | 69.46 |
| wt % $C_9$+ Selectivity*** | 6.42 | 7.10 |

As used herein, the term about means within 10% of the value, or within 5%, or within 1%.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed:

1. An alkylation process comprising:
   passing an isoparaffin having from 4 to 10 carbon atoms and an olefin having from 3 to 10 carbon atoms to an alkylation reactor containing an unsupported, halometallate based ionic liquid catalyst to generate an alkylate having a research octane number of at least about 93,
   wherein the ionic liquid catalyst has an initial kinematic viscosity in a range of about 50 cSt to about 100 cSt at a temperature of 25° C., and
   wherein the alkylation reactor is operated at reaction conditions comprising an operating temperature greater than about 20° C., a molar ratio of isoparaffin to olefin of less than about 20:1, an overall olefin feed rate of greater than about 8 mol olefin/mol ionic liquid catalyst/hr, and a total residence time in a range of about 1 min to about 10 min.

2. The process of claim 1 wherein the ionic liquid catalyst has the initial kinematic viscosity in the range of about 60 cSt to about 90 cSt at a temperature of 25° C.

3. The process of claim 1 wherein the ionic liquid catalyst has an initial kinematic viscosity in a range of about 30 cSt to about 60 cSt at a temperature of 38° C.

4. The process of claim 1 wherein the operating temperature is in a range of about 20° C. to about 30° C.

5. The process of claim 4 wherein the isoparaffin has 4 carbon atoms and the olefin has 4 carbon atoms, wherein the reaction has a selectivity for C8 of at least about 67%, and wherein the alkylate has a mole ratio of trimethylpentane to dimethylhexane of greater than about 12.

6. The process of claim 4 wherein the alkylate has a research octane number of at least about 95.

7. The process of claim 1 wherein the operating temperature is greater than about 30° C.

8. The process of claim 7 wherein the isoparaffin has 4 carbon atoms and the olefin has 4 carbon atoms, wherein the reaction has a selectivity for C8 of at least about 65%, and wherein the alkylate has a mole ratio of trimethylpentane to dimethylhexane of greater than about 7.

9. The process of claim 1 wherein the ionic liquid catalyst comprises a phosphonium based ionic liquid, an imidazolium based ionic liquid having long side chains, a pyridinium based ionic liquid having long side chains, an ammonium based ionic liquid having long side chains, an imidazolium based ionic liquid having a brominated anion, a pyridinium based ionic liquid having a brominated anion, an ammonium based ionic liquid having a brominated anion, imidazolium, pyridinium, ammonium based ionic liquids with halometallate anions having an anion to cation ratio greater than 1.5 and less than 2, or combinations thereof.

10. The process of claim 1 wherein the ionic liquid catalyst is tributylpentylphosphonium heptachloroaluminate, tripropylhexylphosphonium heptachloroaluminate, tributylmethylphosphonium heptachloroaluminate, benzyltrimethylammonium heptachloroaluminates, tetrabutylphosphonium heptachloroaluminate, or combinations thereof.

11. The process of claim 1 wherein a conversion of the olefin is at least about 96%.

12. An alkylation process comprising:
passing an isoparaffin having 4 carbon atoms and an olefin having 4 carbon atoms to an alkylation reactor containing an unsupported, halometallate based ionic liquid catalyst to generate an alkylate,
wherein the ionic liquid catalyst has an initial kinematic viscosity in a range of about 50 cSt to about 100 cSt at a temperature of 25° C.,
wherein the alkylation reactor is operated at reaction conditions comprising an operating temperature greater than about 20° C., a molar ratio of isoparaffin to olefin of less than about 20:1, an overall olefin feed rate of greater than about 8 mol olefin/mol ionic liquid catalyst/hr, and a total residence time in a range of about 1 min to about 10 min,
wherein the reaction has a selectivity for C8 of at least about 65%, and
wherein the alkylate has a mole ratio of trimethylpentane to dimethylhexane of greater than 7:1.

13. The process of claim 12 wherein the ionic liquid catalyst has an initial kinematic viscosity in a range of about 30 cSt to about 60 cSt at a temperature of 38° C.

14. The process of claim 12 wherein the operating temperature is in a range of about 20° C. to about 30° C.

15. The process of claim 14 wherein the reaction has a selectivity for C8 of at least about 67%, wherein the alkylate has a mole ratio of trimethylpentane to dimethylhexane of greater than about 12:1, and wherein the alkylate has a research octane number of at least about 95.

16. The process of claim 12 wherein the operating temperature is greater than about 30° C.

17. The process of claim 16 wherein the reaction has a selectivity for C8 of at least about 65%, and wherein the alkylate has a research octane number of at least about 93.

18. The process of claim 12 wherein the ionic liquid catalyst comprises a phosphonium based ionic liquid, an imidazolium based ionic liquid having long side chains, a pyridinium based ionic liquid having long side chains, an ammonium based ionic liquid having long side chains, an imidazolium based ionic liquid having a brominated anion, a pyridinium based ionic liquid having a brominated anion, an ammonium based ionic liquid having a brominated anion, or combinations thereof.

19. The process of claim 12 wherein the ionic liquid catalyst comprises tributylpentylphosphonium heptachloroaluminate, tripropylhexylphosphonium heptachloroaluminate, tributylmethylphosphonium heptachloroaluminate, benzyltrimethylammonium heptachloroaluminates, tetrabutylphosphonium heptachloroaluminate, or combinations thereof.

20. The process of claim 12 wherein a conversion of the olefin is at least about 96%.

* * * * *